(12) United States Patent
Koo et al.

(10) Patent No.: US 9,288,886 B2
(45) Date of Patent: Mar. 15, 2016

(54) PLASMA-BASED CHEMICAL SOURCE DEVICE AND METHOD OF USE THEREOF

(75) Inventors: Il-Gyo Koo, Fort Collins, CO (US); Cameron A. Moore, Loveland, CO (US); George J. Collins, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 318 days.

(21) Appl. No.: 12/995,106

(22) PCT Filed: May 29, 2009

(86) PCT No.: PCT/US2009/045708
§ 371 (c)(1),
(2), (4) Date: Feb. 18, 2011

(87) PCT Pub. No.: WO2009/146432
PCT Pub. Date: Dec. 3, 2009

(65) Prior Publication Data
US 2011/0139751 A1    Jun. 16, 2011

Related U.S. Application Data

(60) Provisional application No. 61/057,667, filed on May 30, 2008.

(51) Int. Cl.
| | |
|---|---|
| *H05H 1/24* | (2006.01) |
| *H01J 37/32* | (2006.01) |
| *A61B 18/04* | (2006.01) |
| *C23C 16/513* | (2006.01) |

(52) U.S. Cl.
CPC ............... *H05H 1/24* (2013.01); *A61B 18/042* (2013.01); *H01J 37/3255* (2013.01); *H01J 37/32348* (2013.01); *H05H 1/2406* (2013.01); *C23C 16/513* (2013.01); *H05H 2001/245* (2013.01); *H05H 2001/2412* (2013.01); *H05H 2001/2418* (2013.01); *H05H 2001/2431* (2013.01); *H05H 2001/2443* (2013.01)

(58) Field of Classification Search
CPC ................. A61B 18/042; A61B 18/06; A61B 2017/00747; A61B 2017/00761; A61B 2018/00452; A61B 2018/00571–2018/0063; A61B 2018/00702; A61B 2018/00726; A61B 2018/1213; A61B 2018/122; A61B 2018/162; A61B 2018/1807; A61B 2018/0091–2018/00958; A61B 2018/062–2018/068; A61B 2018/0072; A61L 2/10; A61L 2/14; B01J 19/088; B01J 19/123; B01J 2219/0809; B01J 2219/083; B01J 2219/0847; B01J 2219/0894; B01J 2219/0896; B01J 2219/0898; C22B 4/005; C22B 9/226; C23C 16/30; C23C 16/513; H01J 11/12; H01J 2237/0815; H01J 2237/338; H01J 37/32009; H01J 37/32018; H01J 37/32357; H01J 37/32366; H01J 37/3244; H01J 37/32449; H01J 37/32596; H01J 61/0672; H01J 65/046; H01J 37/32082; H01J 37/32348; H01J 37/32431; H01J 37/32541; H01J 37/3255; H01J 2240/10; H01J 2245/12–2245/125; H01J 37/32532; H05H 1/24; H05H 1/2406; H05H 1/30; H05H 1/34; H05H 1/42; H05H 2001/2443; H05H 2001/2456; H05H 2001/2462; H05H 2001/3431; H05H 2001/2412–2001/2437; H05H 2001/245–2001/2468; H05H 2240/10–2240/20; H05H 2245/12–2245/125; H05H 2001/24512; H05H 2001/2418; H05H 2001/2431; H05H 2245/122; A61C 19/00; A61C 19/06; B05D 1/62

USPC ............ 118/723 E, 723 ER, 732 R, 723 MP, 118/723 ME, 726, 695, 696, 723 R, 118/715, 720, 723 IR; 156/345.44, 345.24, 156/345.47, 345.48, 345.49, 345.33, 345.3, 156/345.43; 216/67; 250/423 R, 424, 425, 250/426, 423 F; 427/569; 604/19, 22, 23, 604/24, 25; 606/9, 20, 23, 25, 34, 39, 40, 606/41, 45, 48, 49, 50; 607/100, 101; 422/1, 4, 21, 186, 186.01, 186.03, 422/186.4, 186.5

See application file for complete search history.

U.S. PATENT DOCUMENTS

| | | | |
|---|---|---|---|
| 438,257 A | 10/1890 | Raquet | |
| 2,213,820 A | 9/1940 | Maxson | |
| 2,598,301 A | 5/1952 | Rajchman | |
| 3,134,947 A | 5/1964 | Charasz | |
| 3,308,050 A * | 3/1967 | Denis et al. | 422/186.03 |
| 3,434,476 A * | 3/1969 | Shaw et al. | 606/22 |
| 3,492,074 A * | 1/1970 | Rendina | 356/316 |
| 3,687,832 A * | 8/1972 | Fydelor et al. | 204/165 |
| 3,838,242 A | 9/1974 | Goucher | |
| 3,903,891 A | 9/1975 | Brayshaw | |
| 3,938,525 A | 2/1976 | Coucher | |
| 4,010,400 A | 3/1977 | Hollister | |
| 4,017,707 A | 4/1977 | Brown et al. | |
| 4,143,337 A | 3/1979 | Beaulieu | |
| 4,177,422 A | 12/1979 | Deficis et al. | |
| 4,181,897 A | 1/1980 | Miller | |
| 4,188,426 A * | 2/1980 | Auerbach | 427/490 |
| 4,274,919 A | 6/1981 | Jensen et al. | |
| 4,337,415 A | 6/1982 | Dürr | |
| 4,517,495 A * | 5/1985 | Piepmeier | 315/111.21 |
| 4,577,165 A | 3/1986 | Uehara et al. | |
| 4,629,887 A | 12/1986 | Bernier | |
| 4,629,940 A | 12/1986 | Gagne et al. | |
| 4,699,082 A * | 10/1987 | Hakim | 118/716 |
| 4,780,803 A | 10/1988 | Dede Garcia-Santamaria | |
| 4,781,175 A * | 11/1988 | McGreevy et al. | 606/40 |
| 4,818,916 A | 4/1989 | Morrisroe | |
| 4,837,484 A * | 6/1989 | Eliasson et al. | 313/634 |
| 4,877,999 A | 10/1989 | Knapp et al. | |
| 4,901,719 A | 2/1990 | Trenconsky et al. | |
| 4,922,210 A | 5/1990 | Flachenecker et al. | |
| 4,956,582 A | 9/1990 | Bourassa | |
| 5,013,959 A * | 5/1991 | Kogelschatz | 313/36 |
| 5,025,373 A | 6/1991 | Keyser, Jr. et al. | |
| 5,041,110 A * | 8/1991 | Fleenor | 606/34 |
| 5,098,430 A | 3/1992 | Fleenor | |
| 5,117,088 A * | 5/1992 | Stava | 219/137 PS |
| 5,124,526 A | 6/1992 | Muller et al. | |
| 5,135,604 A | 8/1992 | Kumar et al. | |
| 5,155,547 A | 10/1992 | Casper et al. | |
| 5,159,173 A | 10/1992 | Frind et al. | |
| 5,180,949 A | 1/1993 | Durr | |
| 5,194,740 A * | 3/1993 | Kogelschatz et al. | 250/492.1 |
| 5,223,457 A | 6/1993 | Mintz et al. | |
| 5,256,138 A | 10/1993 | Burek et al. | |
| 5,280,154 A | 1/1994 | Cuomo et al. | |
| 5,300,068 A | 4/1994 | Rosar et al. | |
| 5,304,279 A | 4/1994 | Coultas et al. | |
| 5,320,621 A | 6/1994 | Gordon et al. | |
| 5,334,834 A | 8/1994 | Ito et al. | |
| RE34,780 E | 11/1994 | Trenconsky et al. | |
| 5,383,019 A | 1/1995 | Farrell et al. | |
| 5,384,167 A | 1/1995 | Nishiwaki et al. | |
| 5,401,350 A | 3/1995 | Patrick et al. | |
| 5,449,356 A | 9/1995 | Walbrink et al. | |
| 5,449,432 A | 9/1995 | Hanawa | |
| 5,466,424 A * | 11/1995 | Kusano et al. | 422/186.05 |
| 5,505,729 A | 4/1996 | Rau | |
| 5,526,138 A | 6/1996 | Sato | |
| 5,534,231 A | 7/1996 | Savas | |
| 5,607,509 A | 3/1997 | Schumacher et al. | |
| 5,618,382 A | 4/1997 | Mintz et al. | |
| 5,683,366 A | 11/1997 | Eggers et al. | |
| 5,688,357 A | 11/1997 | Hanawa | |
| 5,697,882 A | 12/1997 | Eggers et al. | |
| 5,708,330 A | 1/1998 | Rothenbuhler et al. | |
| 5,720,745 A | 2/1998 | Farin et al. | |
| 5,733,511 A | 3/1998 | De Francesco | |
| 5,776,255 A * | 7/1998 | Asaba et al. | 118/726 |
| 5,780,862 A * | 7/1998 | Siess | 250/492.3 |
| 5,810,764 A | 9/1998 | Eggers et al. | |
| 5,818,581 A | 10/1998 | Kurosawa et al. | |
| 5,841,531 A | 11/1998 | Gliddon | |
| 5,843,019 A | 12/1998 | Eggers et al. | |
| 5,843,079 A | 12/1998 | Suslov | |
| 5,845,488 A | 12/1998 | Hancock et al. | |
| 5,849,136 A | 12/1998 | Mintz et al. | |
| 5,858,477 A | 1/1999 | Veerasamy et al. | |
| 5,865,937 A | 2/1999 | Shan et al. | |
| 5,866,985 A | 2/1999 | Coultas et al. | |
| 5,869,832 A * | 2/1999 | Wang et al. | 250/288 |
| 5,892,328 A | 4/1999 | Shang et al. | |
| 5,909,086 A | 6/1999 | Kim et al. | |
| 5,945,790 A * | 8/1999 | Schaefer | 315/335 |
| 5,955,886 A * | 9/1999 | Cohen et al. | 324/464 |
| 5,961,772 A | 10/1999 | Selwyn | |
| 5,977,715 A | 11/1999 | Li et al. | |
| 6,013,075 A | 1/2000 | Avramenko et al. | |
| 6,020,794 A | 2/2000 | Wilbur | |
| 6,024,733 A | 2/2000 | Eggers et al. | |
| 6,027,601 A | 2/2000 | Hanawa | |
| 6,027,617 A * | 2/2000 | Hayashi et al. | 204/170 |
| 6,030,667 A | 2/2000 | Nakagawa et al. | |
| 6,033,582 A | 3/2000 | Lee et al. | |
| 6,036,878 A | 3/2000 | Collins | |
| 6,046,546 A | 4/2000 | Porter et al. | |
| 6,047,700 A | 4/2000 | Eggers et al. | |
| 6,053,172 A | 4/2000 | Hovda et al. | |
| 6,063,079 A | 5/2000 | Hovda et al. | |
| 6,063,084 A | 5/2000 | Farin | |
| 6,063,937 A | 5/2000 | Dlubala et al. | |
| 6,066,134 A | 5/2000 | Eggers et al. | |
| 6,086,585 A | 7/2000 | Hovda et al. | |
| 6,099,523 A | 8/2000 | Kim et al. | |
| 6,102,046 A | 8/2000 | Weinstein et al. | |
| 6,105,581 A | 8/2000 | Eggers et al. | |
| 6,109,268 A | 8/2000 | Thapliyal et al. | |
| 6,110,395 A | 8/2000 | Gibson, Jr. | |
| 6,113,597 A | 9/2000 | Eggers et al. | |
| 6,132,575 A | 10/2000 | Pandumsoporn et al. | |
| 6,137,237 A | 10/2000 | MacLennan et al. | |
| 6,142,992 A | 11/2000 | Cheng et al. | |
| 6,149,620 A | 11/2000 | Baker et al. | |
| 6,153,852 A * | 11/2000 | Blutke et al. | 219/121.59 |
| 6,159,208 A | 12/2000 | Hovda et al. | |
| 6,170,428 B1 | 1/2001 | Redeker et al. | |
| 6,178,918 B1 | 1/2001 | Van Os et al. | |
| 6,179,836 B1 | 1/2001 | Eggers et al. | |
| 6,182,469 B1 | 2/2001 | Campbell et al. | |
| 6,183,655 B1 | 2/2001 | Wang et al. | |
| 6,190,381 B1 | 2/2001 | Olsen et al. | |
| 6,197,026 B1 | 3/2001 | Farin et al. | |
| 6,203,542 B1 | 3/2001 | Ellsberry et al. | |
| 6,206,871 B1 | 3/2001 | Zanon et al. | |
| 6,206,878 B1 * | 3/2001 | Bishop et al. | 606/49 |
| 6,207,924 B1 | 3/2001 | Trassy | |
| 6,210,402 B1 | 4/2001 | Olsen et al. | |
| 6,210,410 B1 | 4/2001 | Farin et al. | |
| 6,213,999 B1 | 4/2001 | Platt, Jr. et al. | |
| 6,222,186 B1 | 4/2001 | Li et al. | |
| 6,224,592 B1 | 5/2001 | Eggers et al. | |
| 6,225,593 B1 | 5/2001 | Howieson et al. | |
| 6,228,078 B1 | 5/2001 | Eggers et al. | |
| 6,228,082 B1 | 5/2001 | Baker et al. | |
| 6,228,229 B1 | 5/2001 | Raaijmakers et al. | |
| 6,235,020 B1 | 5/2001 | Cheng et al. | |
| 6,237,526 B1 | 5/2001 | Brcka | |
| 6,238,391 B1 | 5/2001 | Olsen et al. | |
| 6,242,735 B1 | 6/2001 | Li et al. | |
| 6,248,250 B1 | 6/2001 | Hanawa et al. | |
| 6,252,354 B1 | 6/2001 | Collins et al. | |
| 6,254,600 B1 | 7/2001 | Willink et al. | |
| 6,254,738 B1 | 7/2001 | Stimson et al. | |
| 6,264,650 B1 | 7/2001 | Hovda et al. | |
| 6,264,651 B1 | 7/2001 | Underwood et al. | |
| 6,264,652 B1 | 7/2001 | Eggers et al. | |
| 6,270,687 B1 | 8/2001 | Ye et al. | |
| 6,277,112 B1 | 8/2001 | Underwood et al. | |
| 6,277,251 B1 | 8/2001 | Hwang et al. | |
| 6,283,961 B1 | 9/2001 | Underwood et al. | |
| 6,287,980 B1 | 9/2001 | Hanazaki et al. | |
| 6,291,938 B1 | 9/2001 | Jewett et al. | |
| 6,296,636 B1 | 10/2001 | Cheng et al. | |
| 6,296,638 B1 | 10/2001 | Davison et al. | |
| 6,299,948 B1 | 10/2001 | Gherardi et al. | |
| 6,309,387 B1 | 10/2001 | Eggers et al. | |

| Patent | Kind | Date | Inventor | Ref |
|---|---|---|---|---|
| 6,313,587 | B1 | 11/2001 | MacLennan et al. | |
| 6,326,584 | B1 | 12/2001 | Jewett et al. | |
| 6,326,739 | B1 | 12/2001 | MacLennan et al. | |
| 6,328,760 | B1 | 12/2001 | James | |
| 6,329,757 | B1 | 12/2001 | Morrisroe et al. | |
| 6,333,481 | B2 | 12/2001 | Augeraud et al. | |
| 6,345,588 | B1 | 2/2002 | Stimson | |
| 6,346,108 | B1 | 2/2002 | Fischer | |
| 6,348,051 | B1 | 2/2002 | Farin et al. | |
| 6,353,206 | B1 | 3/2002 | Roderick | |
| 6,355,032 | B1 | 3/2002 | Hovda et al. | |
| 6,363,937 | B1 | 4/2002 | Hovda et al. | |
| 6,365,063 | B2 | 4/2002 | Collins et al. | |
| 6,365,864 | B1 * | 4/2002 | Stava | 219/50 |
| 6,375,750 | B1 | 4/2002 | Van Os et al. | |
| 6,376,972 | B1 * | 4/2002 | Tarasenko et al. | 313/231.01 |
| 6,379,351 | B1 | 4/2002 | Thapliyal et al. | |
| 6,387,088 | B1 | 5/2002 | Shattuck et al. | |
| 6,391,025 | B1 | 5/2002 | Weinstein et al. | |
| 6,396,214 | B1 | 5/2002 | Grosse et al. | |
| 6,401,652 | B1 | 6/2002 | Mohn et al. | |
| 6,407,513 | B1 * | 6/2002 | Vollkommer et al. | 315/246 |
| 6,409,933 | B1 | 6/2002 | Holland et al. | |
| RE37,780 | E | 7/2002 | Lanzani et al. | |
| 6,416,507 | B1 | 7/2002 | Eggers et al. | |
| 6,416,508 | B1 | 7/2002 | Eggers et al. | |
| 6,416,633 | B1 | 7/2002 | Spence | |
| 6,419,752 | B1 * | 7/2002 | Shvets et al. | 118/720 |
| 6,424,099 | B1 | 7/2002 | Kirkpatrick et al. | |
| 6,424,232 | B1 | 7/2002 | Mavretic et al. | |
| 6,429,400 | B1 * | 8/2002 | Sawada et al. | 219/121.52 |
| 6,432,103 | B1 | 8/2002 | Ellsberry et al. | |
| 6,432,260 | B1 | 8/2002 | Mahoney et al. | |
| 6,443,948 | B1 | 9/2002 | Suslov | |
| 6,444,084 | B1 | 9/2002 | Collins | |
| 6,445,141 | B1 | 9/2002 | Kastner et al. | |
| 6,459,066 | B1 | 10/2002 | Khater et al. | |
| 6,461,350 | B1 | 10/2002 | Underwood et al. | |
| 6,461,354 | B1 | 10/2002 | Olsen et al. | |
| 6,464,695 | B2 | 10/2002 | Hovda et al. | |
| 6,464,889 | B1 | 10/2002 | Lee et al. | |
| 6,464,891 | B1 | 10/2002 | Druz et al. | |
| 6,468,270 | B1 | 10/2002 | Hovda et al. | |
| 6,468,274 | B1 | 10/2002 | Alleyne et al. | |
| 6,471,822 | B1 | 10/2002 | Yin et al. | |
| 6,474,258 | B2 | 11/2002 | Brcka | |
| 6,475,215 | B1 * | 11/2002 | Tanrisever | 606/45 |
| 6,482,201 | B1 | 11/2002 | Olsen et al. | |
| 6,488,825 | B1 * | 12/2002 | Hilliard | 204/298.06 |
| 6,497,826 | B2 | 12/2002 | Li et al. | |
| 6,500,173 | B2 | 12/2002 | Underwood et al. | |
| 6,501,079 | B1 * | 12/2002 | Furuya | 250/437 |
| 6,502,416 | B2 | 1/2003 | Kawasumi et al. | |
| 6,502,588 | B2 | 1/2003 | Li et al. | |
| 6,504,307 | B1 * | 1/2003 | Malik et al. | 315/111.21 |
| 6,507,155 | B1 | 1/2003 | Barnes et al. | |
| 6,525,481 | B1 | 2/2003 | Klima et al. | |
| 6,534,133 | B1 * | 3/2003 | Kaloyeros et al. | 427/576 |
| 6,540,741 | B1 | 4/2003 | Underwood et al. | |
| 6,544,261 | B2 | 4/2003 | Ellsberry et al. | |
| 6,565,558 | B1 | 5/2003 | Lindenmeier et al. | |
| 6,575,968 | B1 | 6/2003 | Eggers et al. | |
| 6,579,289 | B2 | 6/2003 | Schnitzler | |
| 6,579,426 | B1 | 6/2003 | Van Gogh et al. | |
| 6,582,423 | B1 | 6/2003 | Thapliyal et al. | |
| 6,582,427 | B1 | 6/2003 | Goble et al. | |
| 6,582,429 | B2 | 6/2003 | Krishnan et al. | |
| 6,589,237 | B2 | 7/2003 | Woloszko et al. | |
| 6,589,437 | B1 | 7/2003 | Collins | |
| 6,595,990 | B1 | 7/2003 | Weinstein et al. | |
| 6,617,794 | B2 | 9/2003 | Barnes et al. | |
| 6,624,583 | B1 | 9/2003 | Coll et al. | |
| 6,625,555 | B2 | 9/2003 | Kuan et al. | |
| 6,629,974 | B2 | 10/2003 | Penny et al. | |
| 6,632,193 | B1 | 10/2003 | Davison et al. | |
| 6,632,220 | B1 | 10/2003 | Eggers et al. | |
| 6,642,526 | B2 | 11/2003 | Hartley | |
| 6,646,386 | B1 | 11/2003 | Sirkis et al. | |
| 6,652,717 | B1 | 11/2003 | Hong | |
| 6,653,594 | B2 | 11/2003 | Nakamura et al. | |
| 6,659,106 | B1 | 12/2003 | Hovda et al. | |
| 6,663,017 | B2 | 12/2003 | Endres et al. | |
| 6,685,803 | B2 | 2/2004 | Lazarovich et al. | |
| 6,700,093 | B2 * | 3/2004 | Chiou et al. | 219/121.55 |
| 6,712,811 | B2 | 3/2004 | Underwood et al. | |
| 6,719,754 | B2 | 4/2004 | Underwood et al. | |
| 6,719,883 | B2 | 4/2004 | Stimson | |
| 6,723,091 | B2 | 4/2004 | Goble et al. | |
| 6,726,684 | B1 | 4/2004 | Woloszko et al. | |
| 6,740,842 | B2 | 5/2004 | Johnson et al. | |
| 6,746,447 | B2 | 6/2004 | Davison et al. | |
| 6,763,836 | B2 | 7/2004 | Tasto et al. | |
| 6,770,071 | B2 | 8/2004 | Woloszko et al. | |
| 6,772,012 | B2 | 8/2004 | Ricart et al. | |
| 6,773,431 | B2 | 8/2004 | Eggers et al. | |
| 6,774,569 | B2 | 8/2004 | De Vries et al. | |
| 6,780,178 | B2 | 8/2004 | Palanker et al. | |
| 6,780,184 | B2 | 8/2004 | Tanrisever | |
| 6,781,317 | B1 | 8/2004 | Goodman | |
| 6,787,730 | B2 | 9/2004 | Coccio et al. | |
| 6,805,130 | B2 | 10/2004 | Tasto et al. | |
| 6,806,438 | B2 | 10/2004 | Nakano et al. | |
| 6,815,633 | B1 | 11/2004 | Chen et al. | |
| 6,818,140 | B2 | 11/2004 | Ding | |
| 6,832,996 | B2 | 12/2004 | Woloszko et al. | |
| 6,837,884 | B2 | 1/2005 | Woloszko | |
| 6,837,887 | B2 | 1/2005 | Woloszko et al. | |
| 6,837,888 | B2 | 1/2005 | Ciarrocca et al. | |
| 6,840,937 | B2 | 1/2005 | Van Wyk | |
| 6,849,191 | B2 | 2/2005 | Ono et al. | |
| 6,855,143 | B2 | 2/2005 | Davison et al. | |
| 6,855,225 | B1 | 2/2005 | Su et al. | |
| 6,861,377 | B1 | 3/2005 | Hirai et al. | |
| 6,867,859 | B1 | 3/2005 | Powell | |
| 6,876,155 | B2 | 4/2005 | Howald et al. | |
| 6,890,332 | B2 | 5/2005 | Truckai et al. | |
| 6,896,672 | B1 | 5/2005 | Eggers et al. | |
| 6,896,674 | B1 | 5/2005 | Woloszko et al. | |
| 6,896,775 | B2 | 5/2005 | Chistyakov | |
| 6,909,237 | B1 | 6/2005 | Park et al. | |
| 6,915,806 | B2 | 7/2005 | Pacek et al. | |
| 6,919,527 | B2 | 7/2005 | Boulos et al. | |
| 6,920,883 | B2 | 7/2005 | Bessette et al. | |
| 6,921,398 | B2 | 7/2005 | Carmel et al. | |
| 6,922,093 | B2 | 7/2005 | Kanda | |
| 6,924,455 | B1 | 8/2005 | Chen et al. | |
| 6,929,640 | B1 | 8/2005 | Underwood et al. | |
| 6,949,096 | B2 | 9/2005 | Davison et al. | |
| 6,949,887 | B2 | 9/2005 | Kirkpatrick et al. | |
| 6,958,063 | B1 | 10/2005 | Soll et al. | |
| 6,974,453 | B2 | 12/2005 | Woloszko et al. | |
| 6,991,631 | B2 | 1/2006 | Woloszko et al. | |
| 7,004,941 | B2 | 2/2006 | Tvinnereim et al. | |
| 7,019,253 | B2 | 3/2006 | Johnson et al. | |
| 7,046,088 | B2 | 5/2006 | Ziegler | |
| 7,048,733 | B2 | 5/2006 | Hartley et al. | |
| 7,070,596 | B1 | 7/2006 | Woloszko et al. | |
| 7,084,832 | B2 | 8/2006 | Pribyl | |
| 7,090,672 | B2 | 8/2006 | Underwood et al. | |
| 7,096,819 | B2 | 8/2006 | Chen et al. | |
| 7,100,532 | B2 | 9/2006 | Pribyl | |
| 7,104,986 | B2 | 9/2006 | Hovda et al. | |
| 7,115,185 | B1 | 10/2006 | Gonzalez et al. | |
| 7,122,035 | B2 | 10/2006 | Canady | |
| 7,122,965 | B2 | 10/2006 | Goodman | |
| 7,131,969 | B1 | 11/2006 | Hovda et al. | |
| 7,132,620 | B2 | 11/2006 | Coelho et al. | |
| 7,132,996 | B2 | 11/2006 | Evans et al. | |
| 7,150,745 | B2 | 12/2006 | Stern et al. | |
| 7,157,857 | B2 | 1/2007 | Brouk et al. | |
| 7,160,521 | B2 | 1/2007 | Porshnev et al. | |
| 7,161,112 | B2 | 1/2007 | Smith et al. | |
| 7,164,484 | B2 | 1/2007 | Takahashi et al. | |
| 7,166,816 | B1 | 1/2007 | Chen et al. | |
| 7,179,255 | B2 | 2/2007 | Lettice et al. | |
| 7,186,234 | B2 | 3/2007 | Dahla et al. | |
| 7,189,939 | B2 | 3/2007 | Lee et al. | |
| 7,189,940 | B2 | 3/2007 | Kumar et al. | |

| Patent No. | Date | Inventor(s) |
|---|---|---|
| 7,192,428 B2 | 3/2007 | Eggers et al. |
| 7,199,399 B2 | 4/2007 | Chin-Lung et al. |
| 7,201,750 B1 | 4/2007 | Eggers et al. |
| 7,214,280 B2 | 5/2007 | Kumar et al. |
| 7,214,934 B2 | 5/2007 | Stevenson |
| 7,217,268 B2 | 5/2007 | Eggers et al. |
| 7,217,903 B2 | 5/2007 | Bayer et al. |
| 7,220,261 B2 | 5/2007 | Truckai et al. |
| 7,227,097 B2 | 6/2007 | Kumar et al. |
| 7,238,185 B2 | 7/2007 | Palanker et al. |
| 7,241,293 B2 | 7/2007 | Davison |
| 7,270,658 B2 | 9/2007 | Woloszko et al. |
| 7,270,659 B2 | 9/2007 | Ricart et al. |
| 7,270,661 B2 | 9/2007 | Dahla et al. |
| 7,271,363 B2 | 9/2007 | Lee et al. |
| 7,275,344 B2 | 10/2007 | Woodmansee, III et al. |
| 7,276,063 B2 | 10/2007 | Davison et al. |
| 7,282,244 B2 | 10/2007 | Schaepkens et al. |
| 7,291,804 B2 | 11/2007 | Suslov |
| 7,292,191 B2 | 11/2007 | Anderson |
| 7,297,143 B2 | 11/2007 | Woloszko et al. |
| 7,297,145 B2 | 11/2007 | Woloszko et al. |
| 7,298,091 B2 | 11/2007 | Pickard et al. |
| 7,309,843 B2 | 12/2007 | Kumar et al. |
| 7,316,682 B2 | 1/2008 | Konesky |
| 7,318,823 B2 | 1/2008 | Sharps et al. |
| 7,331,957 B2 | 2/2008 | Woloszko et al. |
| 7,353,771 B2 | 4/2008 | Millner et al. |
| 7,355,379 B2 | 4/2008 | Kitamura et al. |
| 7,357,798 B2 | 4/2008 | Sharps et al. |
| 7,361,175 B2 | 4/2008 | Suslov |
| 7,387,625 B2 | 6/2008 | Hovda et al. |
| 7,393,351 B2 | 7/2008 | Woloszko et al. |
| 7,399,944 B2 | 7/2008 | DeVries et al. |
| 7,410,669 B2 | 8/2008 | Dieckhoff et al. |
| 7,419,488 B2 | 9/2008 | Ciarrocca et al. |
| 7,426,900 B2 | 9/2008 | Brcka |
| 7,429,260 B2 | 9/2008 | Underwood et al. |
| 7,429,262 B2 | 9/2008 | Woloszko et al. |
| 7,431,857 B2 | 10/2008 | Shannon et al. |
| 7,435,247 B2 | 10/2008 | Woloszko et al. |
| 7,442,191 B2 | 10/2008 | Hovda et al. |
| 7,449,021 B2 | 11/2008 | Underwood et al. |
| 7,453,403 B2 | 11/2008 | Anderson |
| 7,459,899 B2 | 12/2008 | Mattaboni et al. |
| 7,468,059 B2 | 12/2008 | Eggers et al. |
| 7,480,299 B2 | 1/2009 | O'Keeffe et al. |
| 7,489,206 B2 | 2/2009 | Kotani et al. |
| 7,491,200 B2 | 2/2009 | Underwood |
| 7,498,000 B2 | 3/2009 | Pekshev et al. |
| 7,506,014 B2 | 3/2009 | Drummond |
| 7,507,236 B2 | 3/2009 | Eggers et al. |
| 7,510,665 B2 | 3/2009 | Shannon et al. |
| 7,511,246 B2 | 3/2009 | Morris roe |
| 7,563,261 B2 | 7/2009 | Carmel et al. |
| 7,566,333 B2 | 7/2009 | Van Wyk et al. |
| 7,589,473 B2 | 9/2009 | Suslov |
| 7,611,509 B2 | 11/2009 | Van Wyk |
| 7,632,267 B2 | 12/2009 | Dahla |
| 7,633,231 B2 | 12/2009 | Watson |
| 7,666,478 B2 | 2/2010 | Paulussen et al. |
| 7,691,101 B2 | 4/2010 | Davison et al. |
| 7,708,733 B2 | 5/2010 | Sanders et al. |
| 7,715,889 B2 | 5/2010 | Ito |
| 7,758,575 B2 | 7/2010 | Beller |
| 7,824,398 B2 | 11/2010 | Woloszko et al. |
| 7,879,034 B2 | 2/2011 | Woloszko et al. |
| 7,887,891 B2 | 2/2011 | Rius |
| 7,892,223 B2 | 2/2011 | Geiselhart |
| 7,892,230 B2 | 2/2011 | Woloszko |
| 7,901,403 B2 | 3/2011 | Woloszko et al. |
| 7,940,008 B2 | 5/2011 | Mattaboni et al. |
| 7,949,407 B2 | 5/2011 | Kaplan et al. |
| 8,994,270 B2* | 3/2015 | Koo et al. ............... 315/111.21 |
| 9,028,656 B2* | 5/2015 | Koo et al. ............... 204/164 |
| 2001/0054601 A1 | 12/2001 | Ding |
| 2002/0014832 A1 | 2/2002 | Moradi et al. |
| 2002/0022836 A1* | 2/2002 | Goble et al. ............... 606/34 |
| 2002/0023899 A1 | 2/2002 | Khater et al. |
| 2002/0092826 A1 | 7/2002 | Ding |
| 2002/0125207 A1 | 9/2002 | Ono et al. |
| 2002/0132380 A1 | 9/2002 | Nakano et al. |
| 2003/0006019 A1 | 1/2003 | Johnson et al. |
| 2003/0036753 A1 | 2/2003 | Morgan et al. |
| 2003/0038912 A1* | 2/2003 | Broer et al. ............... 349/122 |
| 2003/0047540 A1* | 3/2003 | Konavko et al. ........... 219/121.4 |
| 2003/0069576 A1* | 4/2003 | Tanrisever ............... 606/41 |
| 2003/0075522 A1 | 4/2003 | Weichart et al. |
| 2003/0132198 A1 | 7/2003 | Ono et al. |
| 2003/0158545 A1 | 8/2003 | Hovda et al. |
| 2004/0007985 A1 | 1/2004 | De Vries et al. |
| 2004/0022669 A1 | 2/2004 | Ruan et al. |
| 2004/0075375 A1 | 4/2004 | Miyashita et al. |
| 2004/0086434 A1 | 5/2004 | Gadgil et al. |
| 2004/0129212 A1 | 7/2004 | Gadgil et al. |
| 2004/0140194 A1 | 7/2004 | Taylor et al. |
| 2004/0186470 A1* | 9/2004 | Goble et al. ............... 606/41 |
| 2005/0017646 A1 | 1/2005 | Boulos et al. |
| 2005/0103748 A1 | 5/2005 | Yamaguchi et al. |
| 2005/0118350 A1 | 6/2005 | Koulik et al. |
| 2005/0149012 A1 | 7/2005 | Penny et al. |
| 2005/0153159 A1* | 7/2005 | Sugiyama et al. ............ 428/632 |
| 2005/0205212 A1 | 9/2005 | Singh et al. |
| 2005/0236374 A1* | 10/2005 | Blankenship ............ 219/121.11 |
| 2006/0009763 A1* | 1/2006 | Goble et al. ............... 606/49 |
| 2006/0011465 A1 | 1/2006 | Burke et al. |
| 2006/0017388 A1 | 1/2006 | Stevenson |
| 2006/0038992 A1 | 2/2006 | Morrisroe |
| 2006/0065628 A1 | 3/2006 | Vahedi et al. |
| 2006/0091109 A1* | 5/2006 | Partlo et al. ............... 216/63 |
| 2006/0175015 A1 | 8/2006 | Chen et al. |
| 2006/0266735 A1 | 11/2006 | Shannon et al. |
| 2006/0278254 A1 | 12/2006 | Jackson |
| 2007/0021747 A1 | 1/2007 | Suslov |
| 2007/0021748 A1* | 1/2007 | Suslov ............... 606/45 |
| 2007/0027440 A1* | 2/2007 | Altshuler et al. ............... 606/9 |
| 2007/0029292 A1 | 2/2007 | Suslov |
| 2007/0029500 A1* | 2/2007 | Coulombe et al. ......... 250/423 F |
| 2007/0045561 A1* | 3/2007 | Cooper ............... 250/453.11 |
| 2007/0068899 A1* | 3/2007 | Yoon ............... 156/345.43 |
| 2007/0072433 A1* | 3/2007 | Yoon et al. ............... 438/707 |
| 2007/0075652 A1* | 4/2007 | Espiau et al. ............... 315/248 |
| 2007/0084563 A1 | 4/2007 | Holland |
| 2007/0087455 A1 | 4/2007 | Hoffman |
| 2007/0154363 A1* | 7/2007 | Joshi et al. ............... 422/186.04 |
| 2007/0210035 A1 | 9/2007 | Twarog et al. |
| 2007/0251920 A1 | 11/2007 | Hoffman |
| 2007/0258329 A1 | 11/2007 | Winey |
| 2008/0023443 A1 | 1/2008 | Paterson et al. |
| 2008/0050291 A1 | 2/2008 | Nagasawa |
| 2008/0083701 A1 | 4/2008 | Shao et al. |
| 2008/0099434 A1 | 5/2008 | Chandrachood et al. |
| 2008/0099435 A1 | 5/2008 | Grimbergen |
| 2008/0099436 A1 | 5/2008 | Grimbergen |
| 2008/0122252 A1 | 5/2008 | Corke et al. |
| 2008/0179290 A1 | 7/2008 | Collins et al. |
| 2008/0185366 A1 | 8/2008 | Suslov |
| 2008/0268172 A1 | 10/2008 | Fukuda et al. |
| 2008/0284506 A1 | 11/2008 | Messer |
| 2008/0292497 A1 | 11/2008 | Vangeneugden et al. |
| 2009/0039789 A1 | 2/2009 | Nikolay |
| 2009/0039790 A1* | 2/2009 | Suslov ............... 315/111.21 |
| 2009/0054896 A1 | 2/2009 | Fridman et al. |
| 2009/0064933 A1 | 3/2009 | Liu et al. |
| 2010/0089742 A1 | 4/2010 | Suslov |
| 2010/0130973 A1 | 5/2010 | Choi et al. |
| 2011/0101862 A1* | 5/2011 | Koo et al. ............... 315/111.21 |
| 2013/0059273 A1* | 3/2013 | Koo et al. ............... 433/216 |
| 2013/0062014 A1* | 3/2013 | Koo et al. ............... 156/345.11 |
| 2013/0116682 A1* | 5/2013 | Koo et al. ............... 606/41 |
| 2013/0261536 A1* | 10/2013 | Sartor ............... 604/23 |
| 2014/0224643 A1* | 8/2014 | Collins et al. ............... 204/164 |
| 2014/0225495 A1* | 8/2014 | Koo et al. ............... 313/13 |
| 2014/0225498 A1* | 8/2014 | Koo et al. ............... 313/231.31 |

FOREIGN PATENT DOCUMENTS

| | | |
|---|---|---|
| DE | 3710489 | 11/1987 |
| DE | 4139029 | 6/1993 |
| DE | 4326037 | 2/1995 |
| DE | 9117019 | 4/1995 |
| DE | 19537897 | 3/1997 |
| DE | 9117299 | 4/2000 |
| DE | 19848784 | 5/2000 |
| DE | 29724247 | 8/2000 |
| DE | 19524645 | 11/2002 |
| EP | 0016542 B1 | 10/1980 |
| EP | 0 495 699 B1 | 7/1992 |
| EP | 0602764 A1 | 6/1994 |
| EP | 0956827 | 11/1999 |
| EP | 1174901 A2 | 1/2002 |
| FR | 1340509 | 9/1963 |
| JP | 61-159953 | 7/1986 |
| JP | 62-130777 | 6/1987 |
| JP | 03-149797 | 6/1991 |
| JP | H06-119995 A | 4/1994 |
| JP | 8-243755 | 9/1996 |
| JP | 2000-286094 A | 10/2000 |
| JP | 2000286094 A | 10/2000 |
| JP | 2001-501485 A | 2/2001 |
| JP | 2001332399 A | 11/2001 |
| JP | 2003007497 A | 1/2003 |
| JP | 2003049276 A | 2/2003 |
| JP | 2003093869 A | 4/2003 |
| JP | 2005-522824 A | 7/2005 |
| JP | 2005-526904 A | 9/2005 |
| JP | 2005-528737 A | 9/2005 |
| JP | 2005276618 A | 10/2005 |
| JP | 2006114450 A | 4/2006 |
| JP | 2006310101 A | 11/2006 |
| JP | 2007188748 A | 7/2007 |
| JP | 2007207540 A | 8/2007 |
| JP | 2008041495 A | 2/2008 |
| JP | 2008071656 A | 3/2008 |
| JP | 2010-242857 | 10/2010 |
| SU | 1438745 | 11/1988 |
| WO | WO 99/01887 | 1/1999 |
| WO | WO 99/36940 | 7/1999 |
| WO | WO 01/39555 A1 | 5/2001 |
| WO | 03/085693 A1 | 10/2003 |
| WO | 2004032176 A1 | 4/2004 |
| WO | 2004094306 A1 | 11/2004 |
| WO | WO 2006/116252 A2 | 11/2006 |
| WO | WO 2006116828 A1 * | 11/2006 | ............. A61L 2/10 |
| WO | WO 2009036579 A1 * | 3/2009 | ............. H01J 37/32 |
| WO | 2009/146432 A1 | 12/2009 |
| WO | 2010008062 A1 | 1/2010 |

OTHER PUBLICATIONS

Jan-Otto Carlsson "Chemical Vapor Deposition,"Chapter 7 in R.F. Bunshah, Ed., "Handbook of Deposition Technologies for Films and Coatings (2nd Edition)," William Andrew Publishing/Noyes (1994) pp. 400, 411-413 & 457.*

"Fundamentals of Mass Flow Control," Advanced Energy Industries, Inc., Fort Collins, Co. US (2005) pp. 1-5.*

M.I. Lomaev et al., "Capacitive and Barrier Discharge Excilamps and TheirApplications (Review)," Instruments and Experimental Techniques, vol. 49, No. 5, (2006) pp. 595-616.*

E. A. Sosnin et al, "Applications of Capacitive and Barrier Discharge Excilamps in Photoscience," Journal of Photochemistry and Photobiologyh C: Photochemistry Reviews 7 (2006) pp. 145-163.*

V. F. Tarasenko et al. "VUV and UV Excilamps and Their Applications," High Power Laser Ablation VI, edited by C. R. Phipps, Proc. of Society of Photo-Optical Instrumentation Engineers (SPIE) vol. 6261 (2006) 626136.*

T. Oppenlaender et al., "Mercury-free Vacuum-(VUV) andUV Excilamps: Lamps of the Future?" Internation Ultraviolet Assiociation (IUVA) News, vol. 7, No. 4 (20058) pp. 16-20.*

M.I. Lomaev et al., "Exiclamps and Thier Applications (Review)," Progress in Quantum Electornics 36 (2012) 51-97.*

National Instruments Corporation. "LabVIEW(TM): Getting Started with LabVIEW." Apr. 2003 Edition, Part No. 323427-01. pp. i thru i-5 (78 pages). Source location: http://www.ni.com/manuals/. Available: http://www.ni.com/pdf/manuals/323427a.pdf. Accessed: Feb. 27, 2015.*

Valérie Léveillé. "A Miniature Atmospheric Pressure Glow Discharge Torch for Localized Biomedical Applications," Doctoral Thesis, McGill University, Montréal, Canada. 2006. pp. 1-146. Available: http://digitool.Library.McGill.CA:80/R/-?func=dbin-jump-full&object_id=102676&silo_library=GEN01. Accessed: Feb. 25, 2015.*

Sara Yonson. "Cell Treatment and Surface Functionalization Using the Atmospheric Pressure Glow Discharge Plasma Torch (APGD-t)," Masters Thesis, McGill University, Montréal, Canada. 2006. pp. 1-77. Available: http://digitool.Library.McGill.CA:80/R/-?func=dbin-jump-full&object_id=99551&silo_library=GEN01. Accessed: Feb. 26, 2015.*

U.S. Appl. No. 09/270,856, filed Mar. 17, 1999, Gene H. Arts.

U.S. Appl. No. 12/791,100, filed Jun. 1, 2010, Kristin D. Johnson.

U.S. Appl. No. 12/845,842, filed Jul. 29, 2010, Kristin D. Johnson.

Hernandez et al., "A Controlled Study of the Argon Beam Coagultor for Partial Nephrectomy"; The Journal of Urology, vol. 143, (May 1990) J. Urol. 143: pp. 1062-1065.

Ward et al., "A Significant New Contribution to Radical Head and Neck Surgery"; Arch Otolaryngology, Head and Neck Surg., vol. 115 pp. 921-923 (Aug. 1989).

Lieberman et al., "Capacitive Discharges", Principles of Plasma Discharges and Materials Processing, John Wiley & Son, Inc. (2005) pp. 387-460.

Moore et al., "Confined Geometry Interactions of Downstream RF-Excited Atmospheric Plasma Wires", IEEE Transactions on Plasma Science, 0093-3813, (2008) pp. 1-2.

Walsh et al., "Contrasting Characteristics of Pulsed and Sinusoidal Cold Atmospheric Plasma Jets", Applied Physics Letters, 88, 171501 (2006) pp. 1-3.

Cho et al., "Coplanar ac Discharges Between Cylindrical Electrodes With a Nanoporous Alumina Dielectric: Modular Dielectric Barrier Plasma Devices", IEEE Transactions on Plasma Science, vol. 33, No. 2, (Apr. 2005) pp. 378-379.

Xu et al., "DBD Plasma Jet in Atmospheric Pressure Argon", IEEE Transactions on Plasma Science, vol. 36, No. 4, (Aug. 2008), pp. 1352-1353.

Alfred Grill, "Electron Cyclotron Resonance Plasmas", Cold Plasma in Materials Fabrication, IEEE Press (1994) pp. 40-43.

Brand et al., "Electrosurgical Debulking of Ovarian Cancer: A New Technique Using the Argon Beam Coagulator"; Gynecologic Oncology 39 pp. 115-118 (1990).

Grund et al., "Endoscopic Argon Plasma . . . Flexible Endoscopy"; Endoscopic Surgery and Allied Technologies, No. 1, vol. 2, pp. 42-46 (Feb. 1994).

Waye et al., "Endoscopic Treatment Options"; Techniques in Therapeutic Endoscopy, pp. 1.7-1.15, (1987).

B.D. Cullity, "Introduction to Magnetic Materials", University of Notre Dame; Addison-Wesley Publishing Company, Reading MA., (1972) pp. 23-28.

Brian Chapman, "Matching Networks", Glow Discharge Processes, John Wiley & Sons Inc., NY, (1980) pp. 153-172.

Yin et al., "Miniaturization of Inductively Coupled Plasma Sources", IEEE Transactions on Plasma Science, vol. 27, No. 5, (Oct. 1999) pp. 1516-1524.

Park et al., "Nanoporous Anodic Alumina Film on Glass: Improving Transparency by an Ion-Drift Process", Electrochemical and Solid-State Letters, 8 (3) (2005), pp. D5-D7.

P.A. Tulle, "Off-Resonance Microwave-Created Plasmas", Plasma Physics, Pergamon Press (1973) vol. 15, pp. 971-976.

Lieberman et al., "Ohmic Heating", Principles of Plasma Discharges and Materials Processing, John Wiley & Son, Inc. (2005) pp. 97-98.

Lieberman et al., "Optical Actinometry", Principles of Plasma Discharges and Materials Processing, John Wiley & Son, Inc. (2005) pp. 277-279.

Cho et al., "Ozone Production by Nanoporous Dielectric Barrier Glow Discharge in Atmospheric Pressure Air", Applied Physics Letters, 92, 101504, (2008) pp. 1-3.

Lieberman et al., "Particle and Energy Balance in Discharges", Principles of Plasma Discharges and Materials Processing, John Wiley & Son, Inc. (2005) pp. 329-381.
Woloszko et al., "Plasma Characteristics of Repetitively-Pulsed Electrical Discharges in Saline Solutions Used for Surgical Procedures", IEEE Transactions of Plasma Science, vol. 30, No. 3, (Jun. 2002) pp. 1376-1383.
Stoffels et al., "Plasma Needle for In Vivo Medical Treatment: Recent Developments and Perspectives", Plasma Sources Science and Technology 15 (2006) pp. 169-180.
Schaper et al., "Plasma Production and Vapour Layer Production at a Pulse Power Electrode in Saline Solution:", (2008) www.escampig2008.csic.es/PosterSessions/100.
Akitsu et al., "Plasma Sterilization Using Glow Discharge at Atmospheric Pressure", Surface & Coatings Technology 193, (2005) pp. 29-34.
Koo et al., "Room-temperature Slot Microplasma in Atmospheric Pressure Air Between Cylindrical Electrodes With a Nanoporous Alumina Dielectric", Applied Physics Letters, 91, 041502 (2007) pp. 1-3.
Brian Chapman, "Secondary Electron Emission", Glow Discharge Processes, John Wiley & Sons Inc., NY, (1980) pp. 82-138.
Moore et al., "Sensitive, Nonintrusive, In-Situ Measurement of Temporally and Spatially Resolved Plasma Electric Fields", Physical Review Letters, vol. 52, No. 7, (Feb. 13, 1984) pp. 538-541.
Lieberman et al., "Sheaths", Principles of Plasma Discharges and Materials Processing, John Wiley & Son, Inc. (2005) pp. 11-14.
Farin et al., Technology of Argon Plasma . . . Endoscopic Applications; Endoscopic Surgery and Allied Technologies, No. 1, vol. 2, pp. 71-77 (Feb. 1994).
Lieberman et al., "The Collisionless Sheath", Principles of Plasma Discharges and Materials Processing, John Wiley & Son, Inc. (2005) pp. 167-206.
Gupta et al., "The Potential of Pulsed Underwater Streamer Discharges as a Disinfection Technique", IEEE Transactions on Plasma Science, vol. 36, No. 4, (Aug. 2008) pp. 1621-1632.
Mark H. Mellow, "The Role of Endoscopic Laser Therapy in Gastrointestinal Neoplasms"; Advanced Therapeutic Endoscopy, pp. 17-21, (1990).
Silverstein et al., "Thermal Coagulation Therapy for Upper Gastrointestinal Bleeding"; Advanced Therapeutic Endoscopy, pp. 79-84, 1990.
European Search Report EP 01 10 2843.8, dated May 15, 2001.
European Search Report EP 05 00 2257, dated Jun. 1, 2005.
European Search Report EP 05 01 8087, dated Oct. 17, 2005.
European Search Report EP 06 01 9572 dated Nov. 21, 2006.
European Search Report EP 07 00 4356 dated Jul. 2, 2007.
European Search Report EP 07 00 4659 dated Feb. 19, 2008.
European Search Report EP 07 00 4659—partial dated May 24, 2007.
European Search Report EP 09 00 4975 dated Sep. 11, 2009.
European Search Report EP 09 01 0519 dated Nov. 16, 2009.
European Search Report EP 09 01 0520 dated Dec. 10, 2009.
European Search Report EP 09 01 5212.5 dated Apr. 1, 2010.
European Search Report EP 09 17 1599.5 dated Mar. 16, 2010.
European Search Report EP 09 17 1600.1 dated Jan. 26, 2010.
European Search Report EP 10 174107.2 dated Nov. 5, 2010.
European Search Report EP 10 180 912.7 dated Dec. 8, 2010.
European Search Report EP 10 186524.4 dated Feb. 18, 2011.
International Search Report PCT/US98/19284, dated Jan. 14, 1999.
Supplementary European Search Report from Appl. No. EP 09 75 5799 mailed Aug. 31, 2012.
Extended European Search Report issued in Appl. No. 10849146.5 dated Sep. 9, 2013.
Eextended European Search Report corresponding to European Application No. 09755793.8, dated Jul. 21, 2014; 8 pages.
European Serach Report corresponding to European Application No. 09 84 5328, dated Dec. 11, 2014; 8 pages.
European Search Report dated Dec. 9, 2014, corresponding to European Application No. 09 84 5329; 8 pages.
Y. Ushio, et al., "General Film Behaviour 299 Secondary Electron Emission Studies on Mg0 Films," Thin Solid Films, Jan. 1, 1988; pp. 299-308.
Japanese Notice of Final Rejection and Denial of Entry of Amendment (with English translation), issued Apr. 2, 2015, corresponding to Japanese Patent Application No. 2012-513022; 10 total pages.
European Communication/Examination Report dated Jul. 14, 2015, corresponding to European Patent Application No. 09 845 329.3; 8 pages.
European Communication dated Oct. 22, 2015, corresponding to European Application No. 09 755 793.8; 9 pages.
Japanese Office Action (with English translation), dated Nov. 17, 2015, corresponding to Japanese Application No. 2015-009663; 8 total pages.
Extended European Search Report corresponding to European Application No. 09755793.8, dated Jul. 21, 2014; 8 pages.
Japanese Notice of Final Rejection and Denial of Entry of Amendment (with English translation), dated Jun. 2, 2015, corresponding to Japanese Patent Application No. 2013-502548; 15 total pages.
English translation of Japanese Notice of Reasons for Rejection, dated Feb. 18, 2014, corresponding to Japanese Patent Application No. 2013-502548; 6 pages.
English translation of Japanese Notice of Reasons for Rejection, dated Oct. 7, 2014, corresponding to Japanese Patent Application No. 2013-502548; 5 pages.
Australian Patent Examination Report No. 1, dated Apr. 17, 2014, corresponding to Australian Patent Application No. 2010349784; 3 pages.
European Communication dated Jun. 17, 2014, corresponding to European Patent Application No. 10849146.5; 6 pages.
International Search Report, dated Nov. 20, 2009, corresponding to International Patent Applciation No. PCT/US09/05385; 2 pages.
Mark A. Sobolewski, "Current and Voltage Measurements in the Gaseous Electronics Conference RF Reference Cell," Journal of Research of the National Institute of Standards and Technology, vol. 100, No. 4, Jul.-Aug. 1995; pp. 341-351.
International Search Report, dated Dec. 4, 2009, corresponding to International Patent Applciation No. PCT/US09/05389; 2 pages.
International Search Report, dated Apr. 5, 2010, corresponding to International Patent Applciation No. PCT/US09/05398; 2 pages.
International Search Report, dated Nov. 25, 2009, corresponding to International Patent Applciation No. PCT/US09/05389; 2 pages.

* cited by examiner

*Primary Examiner* — Parviz Hassanzadeh
*Assistant Examiner* — Stanislav Antolin

(57) ABSTRACT

The present disclosure provides for a plasma system including a plasma device coupled to a power source, an ionizable media source and a precursor source. During operation, the ionizable media source provides ionizable media and the precursor ionizable media source provides one or more chemical species, photons at specific wavelengths, as well as containing various reactive functional groups and/or components to treat the workpiece surface by working in concert for synergetic selective tissue effects. The chemical species and the ionizable gas are mixed either upstream or midstream from an ignition point of the plasma device and once mixed, are ignited therein under application of electrical energy from the power source. As a result, a plasma effluent and photon source is formed, which carries the ignited plasma feedstock and resulting mixture of reactive species to a workpiece surface to perform a predetermined reaction.

14 Claims, 6 Drawing Sheets

PLASMA-BASED CHEMICAL SOURCE DEVICE AND METHOD OF USE THEREOF

CROSS-REFERENCE TO RELATED APPLICATION

The present application claims the benefit of and priority to U.S. Provisional Application Ser. No. 61/057,667 entitled "PLASMA-BASED CHEMICAL SOURCE DEVICE AND METHOD OF USE THEREOF" filed by Moore et al. on May 30, 2008, the entire contents of which are incorporated by reference herein.

BACKGROUND

1. Technical Field

The present disclosure relates to plasma devices and processes for surface processing and material removal or deposition. More particularly, the disclosure relates to an apparatus and method for generating and directing chemically reactive plasma-generated species in a plasma device along with excited-state species (e.g., energetic photons) that are specific to the selected ingredients.

2. Background of Related Art

Electrical discharges in dense media, such as liquids and gases at or near atmospheric pressure, can, under appropriate conditions, result in plasma formation. Plasmas have the unique ability to create large amounts of chemical species, such as ions, radicals, electrons, excited-state (e.g., metastable) species, molecular fragments, photons, and the like. The plasma species may be generated in a variety of internal energy states or external kinetic energy distributions by tailoring plasma electron temperature and electron density. In addition, adjusting spatial, temporal and temperature properties of the plasma allows for achieving specific changes to the material being irradiated by the plasma species and associated photon fluxes. Plasmas are also capable of generating photons including energetic ultraviolet photons that have sufficient energy to initiate photochemical and photocatalytic reaction paths in biological and other materials that are irradiated by the plasma photons.

SUMMARY

Plasma has broad applicability to provide alternative solutions to industrial, scientific and medical needs, especially workpiece surface processing at low temperature. Plasmas may be delivered to a workpiece, thereby affecting many changes in the properties of materials upon which they impinge. One suitable application of the unique chemical species that are produced is to drive non-equilibrium or selective chemical reactions at the workpiece. Such selective processes are especially sought in biological tissue processing, which allows for cutting and removal of tissue at low temperatures with differential selectivity to underlayers and adjacent tissues. That is, the plasma may remove a distinct upper layer of a workpiece but have little or no effect on a separate underlayer of the workpiece or it may be used to selectively remove a particular tissue from a mixed tissue region or selectively remove a tissue with minimal effect to adjacent organs of different tissue type. More specifically, the plasma species are capable of modifying the chemical nature of tissue surfaces by breaking chemical bonds, substituting or replacing surface-terminating species (e.g., surface functionalization) through volatilization, gasification or dissolution of surface materials (e.g., etching). By proper choices of conditions one can remove a tissue type entirely but not effect a nearby different tissue type at all when selectivity of the plasma chemistry is tailored to be high.

In one aspect, the present disclosure provides for a plasma system including a plasma device coupled to a power source, an ionizable media source and a precursor source. During operation, the ionizable media source provides ionizable media suitable for plasma initiation and maintenance and the precursor source provides one or more chemical species having various reactive functional groups and/or components that are desired for surface treatment. The chemical species and the ionizable media are mixed upstream or at ignition point of the plasma device and, once mixed, are ignited under application of electrical energy from the power source. The ignited media forms a volume of active plasma in the region where electrical energy is delivered. The active plasma volume includes various species that flow therefrom as an effluent that is delivered to a workpiece. Alternatively the species and the ionizable media may be excited separately (e.g., one excited upstream and another added midstream or downstream, which are then combined prior to delivery to a workpiece).

According to one embodiment of the present disclosure, a plasma system is disclosed. The system includes a plasma device having an active electrode and an ionizable media source configured to supply ionizable media to the plasma device. The ionizable media source is coupled to the plasma device at a first connection upstream of the active electrode. The system also includes a precursor source configured to supply at least one precursor feedstock to the plasma device. The precursor source is coupled to the plasma device at a second connection at the active electrode or upstream thereof. The system further includes a power source coupled to the active electrode and configured to ignite the ionizable media and the precursor feedstock at the plasma device to form a plasma volume.

A method for generating plasma is also contemplated by the present disclosure. The method includes the steps of: supplying ionizable media to a plasma device, supplying at least one precursor feedstock to the plasma device at the active electrode or upstream thereof and igniting the ionizable media and the precursor feedstock at the plasma device to form a plasma effluent.

According to another embodiment of the present disclosure, a plasma system is disclosed. The system includes a plasma device having an active electrode and an ionizable media source configured to supply ionizable media to the plasma device. The ionizable media source is coupled to the plasma device at a first connection upstream of the active electrode. The system also includes a plurality of precursor sources, each of the precursor sources is configured to supply at least one precursor feedstock to the plasma device. Each of the precursor sources is also coupled to the plasma device at a second connection at the active electrode or upstream thereof. The system also includes a power source coupled to the active electrode and configured to ignite the ionizable media and the precursor feedstock at the plasma device to form a plasma volume.

BRIEF DESCRIPTION OF THE DRAWINGS

The accompanying drawings, which are incorporated in and constitute a part of this specification, illustrate exemplary embodiments of the disclosure and, together with a general description of the disclosure given above, and the detailed description of the embodiments given below, serve to explain the principles of the disclosure, wherein.

DETAILED DESCRIPTION

Plasmas are commonly generated using electrical energy that is delivered as either direct current (DC) electricity or electricity that is alternating current (AC) at frequencies from about 0.1 hertz (Hz) to about 100 gigahertz (GHz), including radio frequency ("RF", from about 0.1 MHz to about 100 MHz) and microwave ("MW", from about 0.1 GHz to about 100 GHz) bands, using appropriate generators, electrodes, and antennas. Choice of excitation frequency determines many properties and requirements of the plasma, the workpiece, as well as the electrical circuit that is used to deliver electrical energy to the circuit. The performance of the plasma chemical generation and delivery system and the design of the electrical excitation circuitry are interrelated—as the choices of operating voltage, frequency and current levels as well as phase all effect the electron temperature and electron density. Furthermore, choices of electrical excitation and plasma device hardware also determine how a given plasma system responds dynamically to the introduction of new ingredients to the host plasma gas or liquid media and the corresponding dynamic adjustment of the electrical drive, such as via dynamic match networks or adjustments to voltage, current, or excitation frequency to maintain controlled power transfer from the electrical circuit to the plasma.

Figure 1A:
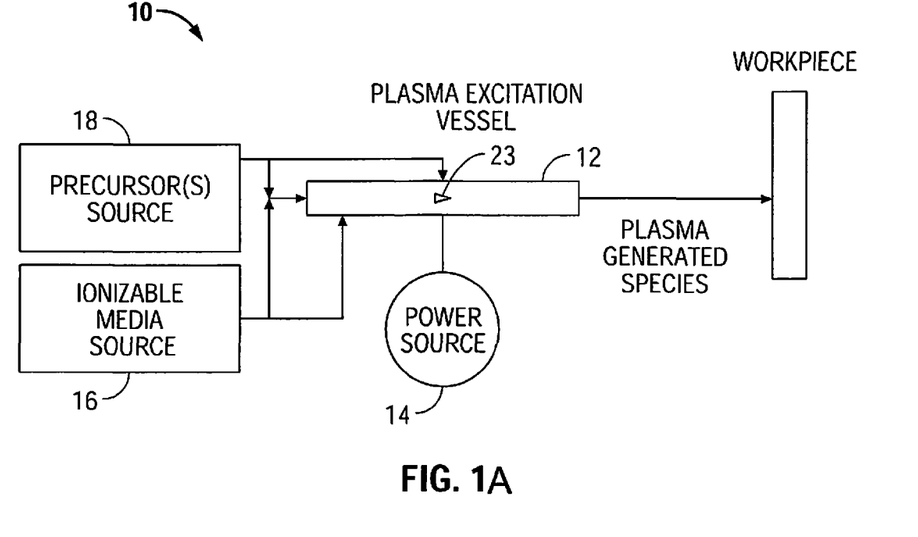
FIG. 1A is a schematic diagram of a plasma system according to the present disclosure.

Referring initially to FIG. 1, a plasma system 10 is disclosed. The system 10 includes a plasma device 12 that is coupled to a power source 14, an ionizable media source 16, and a precursor source 18. Power source 14 includes any required components for delivering power or matching impedance to plasma device 12. More particularly, the power source 14 may be any radio frequency generator or other suitable power source capable of producing power to ignite the ionizable media to generate plasma. The precursor source 18 may be a bubbler or a nebulizer, for aerosolizing precursor feedstocks prior to introduction thereof into the device 12. The precursor source 18 may also be a micro droplet or injector system capable of generating predetermined refined droplet volume of the precursor feedstock from about 1 femtoliter to about 1 nanoliter in volume. The precursor source 18 may also include a microfluidic device, a piezoelectric pump, or an ultrasonic vaporizer.

The system 10 provides a flow of plasma through the device 12 to a workpiece "W" (e.g., tissue). Plasma feedstocks, which include ionizable media and precursor feedstocks, are supplied by the ionizable media source 16 and the precursor source 18, respectively, to the plasma device 12.

During operation, the precursor feedstock and the ionizable media are provided to the plasma device 12 where the plasma feedstocks are ignited to form plasma effluent containing ions, radicals, photons from the specific excited species and metastables that carry internal energy to drive desired chemical reactions in the workpiece "W" or at the surface thereof. The feedstocks may be mixed upstream from the ignition point or midstream thereof (e.g., at the ignition point) of the plasma effluent, as shown in FIG. 1 and described in more detail below.

The ionizable media source 16 provides ionizable feedstock to the plasma device 12. The ionizable media source 16 may include a storage tank and a pump (not explicitly shown) and is coupled to the plasma device 12. The ionizable media may be a liquid or a gas such as argon, helium, neon, krypton, xenon, radon, carbon dioxide, nitrogen, hydrogen, oxygen, etc. and their mixtures, and the like, or a liquid. These and other gases may be initially in a liquid form that is gasified during application.

The precursor source 18 provides precursor feedstock to the plasma device 12. The precursor feedstock may be either in solid, gaseous or liquid form and may be mixed with the ionizable media in any state, such as solid, liquid (e.g., particulates or droplets), gas, and the combination thereof. The precursor source 18 may include a heater, such that if the precursor feedstock is liquid, it may be heated into gaseous state prior to mixing with the ionizable media. In one embodiment, the precursors may be any chemical species capable of forming reactive species such as ions, electrons, excited-state (e.g., metastable) species, molecular fragments (e.g., radicals) and the like, when ignited by electrical energy from the power source 14 or when undergoing collisions with particles (electrons, photons, or other energy-bearing species of limited and selective chemical reactivity) formed from ionizable media 16. More specifically, the precursors may include various reactive functional groups, such as acyl halide, alcohol, aldehyde, alkane, alkene, amide, amine, butyl, carboxlic, cyanate, isocyanate, ester, ether, ethyl, halide, haloalkane, hydroxyl, ketone, methyl, nitrate, nitro, nitrile, nitrite, nitroso, peroxide, hydroperoxide, oxygen, hydrogen, nitrogen, and combination thereof. In embodiments, the chemical precursors may be water, halogenoalkanes, such as dichloromethane, tricholoromethane, carbon tetrachloride, difluoromethane, trifluoromethane, carbon tetrafluoride, and the like; peroxides, such as hydrogen peroxide, acetone peroxide, benzoyl peroxide, and the like; alcohols, such as methanol, ethanol, isopropanol, ethylene glycol, propylene glycol, alkalines such as NaOH, KOH, amines, alkyls, alkenes, and the like. Such chemical precursors may be applied in substantially in pure, mixed, or soluble form.

The precursors and their functional groups may be delivered to a surface to react with the surface species (e.g., molecules) of the workpiece "W." In other words, the functional groups may be used to modify or replace existing surface terminations of the workpiece "W." The functional groups react readily with the surface species due to their high reactivity and the reactivity imparted thereto by the plasma. In addition, the functional groups are also reacted within the plasma volume prior to delivering the plasma volume to the workpiece.

Some functional groups generated in the plasma can be reacted in situ to synthesize materials that subsequently form a deposition upon the surface. This deposition may be used for stimulating healing, killing bacteria, increasing hydration (e.g., adding hydroxyl groups to produce carboxyl group at the workpiece), and increasing hydrophilic or hydroscopic properties. In addition, deposition of certain function groups may also allow for encapsulation of the surface to achieve predetermined gas/liquid diffusion, e.g., allowing gas permeation but preventing liquid exchange, to bond or stimulate bonding of surfaces, or as a physically protective layer.

Figure 2:
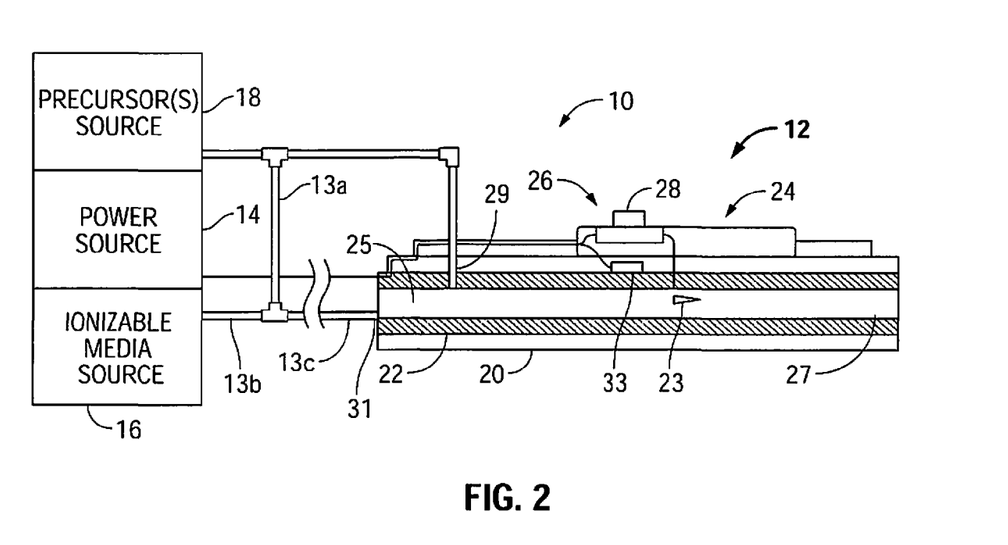
FIG. 2 is a schematic diagram of a plasma system and a plasma handpiece according to one embodiment of the present disclosure.

With reference to FIG. 2, an illustrative embodiment of the plasma device 12 includes a housing 20 enclosing a dielectric inner tube 22 having a proximal end 25 and a distal end 27 configured for the passage of the plasma effluent in either liquid or gaseous form. The plasma device 12 may be utilized as an electrosurgical pencil for application of plasma to tissue and the power source 14 may be an electrosurgical generator that is adapted to supply the device 12 with electrical power at a frequency from about 0.1 MHz to about 1,000 MHz and in another embodiment from about 1 MHz to about 13.6 MHz.

The precursor source 18 and the ionizable media source 16 are coupled to the plasma device 12 via tubing 13a and 13b, respectively, at a first connection 31. The tubing 13a and 13b may be combined into tubing 13c to deliver a mixture of the ionizable media and the precursor feedstock to the device 12. This allows for the plasma feedstocks, e.g., the precursor feedstock and the ionizable gas, to be delivered to the plasma device 12 simultaneously prior to ignition of the mixture therein.

In another embodiment, the ionizable media source 16 and the precursors source 18 may be coupled to the plasma device 12 via the tubing 13a and 13b at separate connections, e.g., the first connection 31 and a second connection 29, respectively, such that the mixing of the feedstocks occurs within the inner tube 22 upstream from ignition point. In other words, the plasma feedstocks are mixed proximally of the ignition point, which may be any point between the respective sources 16 and 18 and the plasma device 12, prior to ignition of the plasma feedstocks to create the desired mix of the plasma effluent species for each specific surface treatment on the workpiece.

Figure 1B:
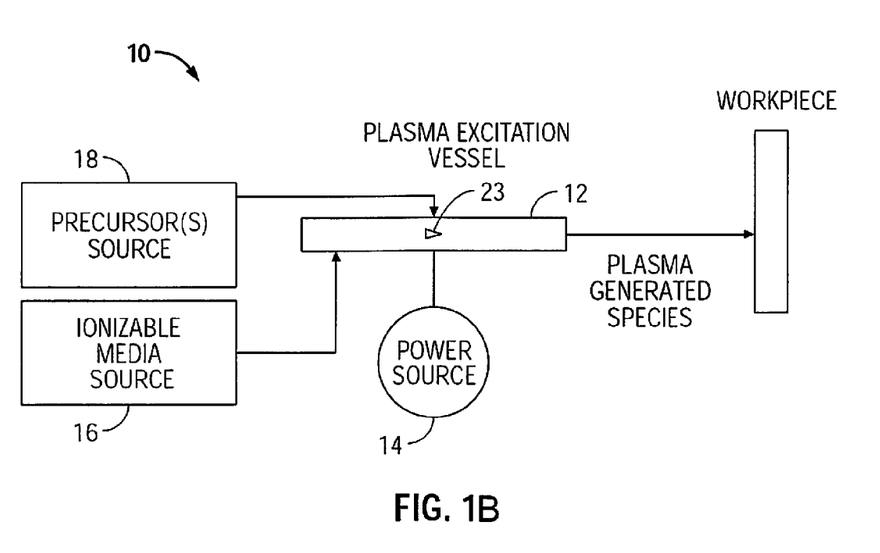
FIG. 1B is a schematic diagram of another embodiment of a plasma system according to the present disclosure.

In a further embodiment, the plasma feedstocks may be mixed midstream, e.g., at the ignition point or downstream of the plasma effluent, directly into the plasma. More specifically, the first and second connections 31, 29 may be coupled to the device 12 at the active electrode 23, such that the precursor feedstocks and the ionizable media are ignited concurrently as they are mixed (FIG. 1B). It is also envisioned that the ionizable media may be supplied to the device 12 proximally of the active electrode 23, while the precursor feedstocks are mixed therewith at the ignition point. In other words, the second connection 29 is coupled to the device 12 at the active electrode to achieve mixing that is concurrent with ignition.

In a further illustrative embodiment, the ionizable media may be ignited in an unimixed state and the precursors may be mixed directly into the ignited plasma. Prior to mixing, the plasma feedstocks may be ignited individually. The plasma feedstock is supplied at a predetermined pressure to create a flow of the medium through the device 12, which aids in the reaction of the plasma feedstocks and produces a plasma effluent.

The device 12 also includes an active electrode 23 that extends around or into tube 22. The device 12 may also include an optional return electrode 33 disposed on an outer surface of the tube 22. The electrodes 23 and 33 are capacitively coupled thereto and to the plasma formed within the tube 22. The electrodes 23 and 33 are formed from a conductive material that may be adapted to assist in the ignition of plasma. In particular, the electrode 23 may have a needle or other pointed shape conducive to maximizing local electric field and forming a predetermined ignition point. The electrodes 23 and 33 are coupled to the power source 14, such that the energy from the power source 14 may be used to ignite the plasma feedstocks flowing through the inner tube 22. In another embodiment electrode 23 is connected to a separate ignition circuit (not shown) that transfers energy to cause ignition of the plasma species.

In yet another illustrative embodiment, the inner tube 22 may also be formed from a conductive material. In this embodiment, the inner tube 22 is coupled to the power source 14 and igniting electrical energy is transmitted directly through the inner tube 22, or between tube 22 and electrode 23. The inner tube 22 and the electrode 23 may be coupled to the power source 14 through a variety of coupling components, such as wires, cables, antennas and the like. Alternatively, the tube 22 and/or the electrode 23 may be fabricated from conductive materials upon which an insulating layer is formed over at least a portion thereof. In one illustrative embodiment, this may be achieved by forming a metal oxide on a conducting metal or by coating an insulating layer on a conductive material.

The inner tube 22 may be coated by a non-reactive material to reduce plasma species loss through undesired surface reactions. Alternatively, the inner tube 22 may be coated by reactive material that may be removed from the inner tube to create plasma species through tailored plasma driven surface reactions including secondary electron emission or volatilized tube construction material(s). The inner tube 22 may also be coated by an optically reflective material that acts as a means to confine photons generated by the plasma.

The inner tube 22 may have a substantially tubular structure (e.g., cylindrical, granular, etc.). In one embodiment, the distal end 27 may have a high aspect ratio cross-section (e.g., oval, rectangular, etc.). This limits and confines the active plasma volume to provide a flattened plasma effluent. The geometrical confinement of the plasma effluent directs the flow of plasma into open air, imparting a directed hydrodynamic flow of effluent to the workpiece "W" to achieve a highly localized effect on the flow boundary layers. This design provides for enhanced control of the hydrodynamic boundary layers of the plasma effluent and thereby isolates the plasma from the user and minimizes the loss of plasma species (e.g., radicals) to open atmosphere due to an extended length of the boundary layer.

The housing 20 also includes a plasma ignition circuit 24, which includes input controls 26 having one or more buttons or switches 28 for activating the circuit 24. The input controls 26 are coupled to the power source 14 and is adapted to activate the energy flow from the power source 14 to the electrodes 23 and 33. More specifically, the input controls 26 signal the power source 14 to provide a minimum voltage and current suitable for igniting the plasma precursor feedstocks flowing through inner tube 22, such that the plasma precursor feedstocks are ignited and plasma effluent is ejected from the distal end 27 of the inner tube 22. This process can be improved upon by enhancing the "Q" factor of the AC power delivery circuit. The activation circuit 24 may be configured either as a toggle switch or a continuous operation switch. In a toggle mode, the plasma effluent is sustained until the switch is toggled. In a continuous mode, the plasma effluent is sustained for as long as the switch is pressed.

In one embodiment, the activation circuit 24 may also be coupled to the ionizable media source 16 and the precursors source 18 such that upon activation of the activation circuit 24, the power source 14 as well as the flow of plasma feedstocks is also activated simultaneously. Those skilled in the art will appreciate that simultaneous activation may include delaying plasma energy from the power source 14 until the plasma feedstocks reach the inner tube 22; this may be accomplished by including flow sensors into the tubing 13 and/or the proximal end 25 of the inner tube 22. Alternatively optical sensors may be used to detect the presence or absence of plasma, or with appropriate optical filtering the presence or absence of one or more particular plasma species. A variety of other upstream and downstream mixing and plasma excitation allows tailoring of the relative concentrations of the various plasma species.

Figure 3:
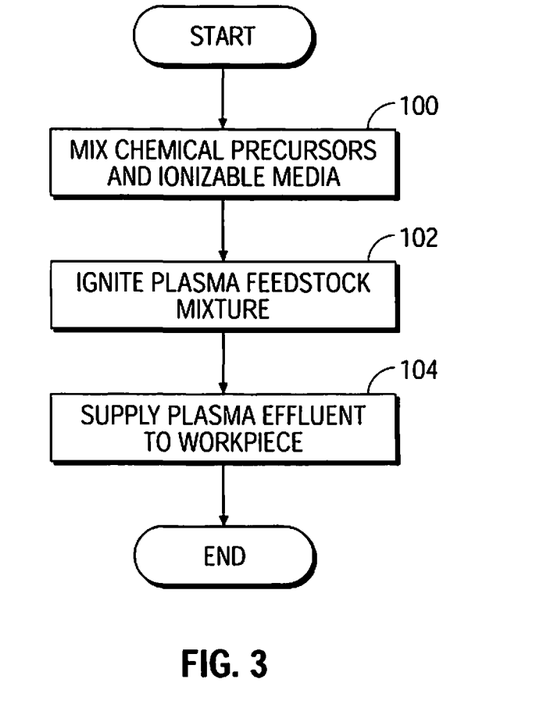
FIG. 3 is a flow diagram of an illustrative method according to the present disclosure.

FIG. 3 illustrates a method for operating the system 10 according to the present disclosure. In step 100, once the plasma device 12 is brought in proximity with the workpiece "W," the activation circuit 24 is activated to commence the flow of the plasma feedstocks from the precursors source 18 and the ionizable media source 16, respectively. The plasma feedstocks are fed to the plasma device 12, where they are mixed upstream prior to ignition thereof or midstream, e.g., in the ignition region. In step 102, the plasma device 12 signals the power source 14 to supply sufficient energy to ignite the mixed plasma feedstocks. The plasma feedstocks are ignited and plasma effluent is sustained by electrical energy. The ignition induces a variety of physical and chemical reactions in the feedstocks, such as dissociation (e.g., breaking up of molecular components into smaller parts) of the feedstocks into highly reactive species (e.g., radicals, ions, etc.). This plasma environment induces chemical changes to the precursors via a multitude of reactions, including direct electron and photon irradiation directly from the ignited plasma. These chemical changes are contrasted to plasma systems that inject precursors downstream from the active plasma volume in that the present disclosure creates said species in much higher densities and at much higher rates. In step 104, the plasma effluent flows out of the distal end 27 of the inner tube 22 to the workpiece "W." The delivered plasma volume includes various reactive species, such as the functional groups of the precursor feedstock, which are deposited unto the workpiece "W" to react with substitutents thereof (e.g., molecules).

Figure 4:
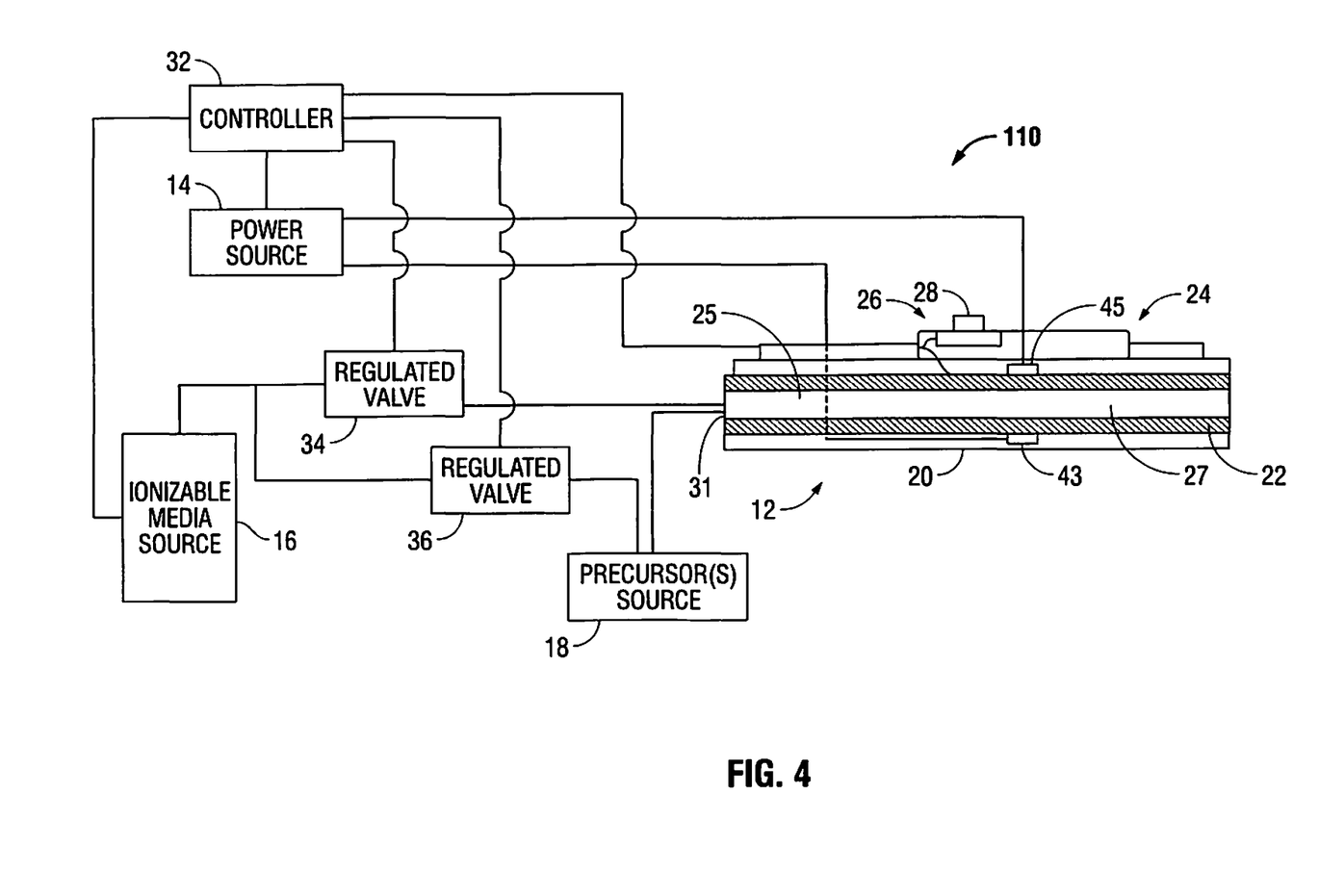
FIG. 4 is a schematic diagram of a plasma system and a plasma handpiece according to one embodiment of the present disclosure.

FIG. 4 illustrates another illustrative embodiment of a plasma system 110. The system 110 includes a controller 32, which may be a microcontroller, microprocessor or any other suitable logic circuit. The controller 32 may be incorporated into the power source 14. The controller 32 may be coupled to the input controls 26 for controlling the system 110. More specifically, the controller 32 is coupled to the power source 14, ionizable media source 16, and first and second regulator valves 34 and 36. The first regulator valve 34 is coupled to the ionizable media source 16 and controls the flow of the ionizable medium to the plasma device 12. The second regulator valve 36 is coupled to the precursor source 18 and controls the flow of the precursors to the plasma device 12.

As shown in FIG. 4, the device 12 includes an active electrode 43 and a return electrode 45 disposed about an outer surface of tube 22. The electrodes 43 are capacitively coupled to the ionizable media and precursor mix in the tube 22 the extent of their relative positions defining the active plasma volume. The operation of the system 110 may be controlled through the input controls 26. The user may initiate the flow of ionizable media source 16 via the input controls 26. The input signal is then processed by the controller 32, which opens the first and second regulator valves 34 and 36 to open the flow of ionizable media and the precursor feedstock. The first and second regulator valves 34 and 36 may be either opened consecutively or simultaneously. The controller 50 then activates the power source 14 in unison with the flow from the first and second regulator valves 34 and 36 as needed to produce metastable plasma.

Figure 5:
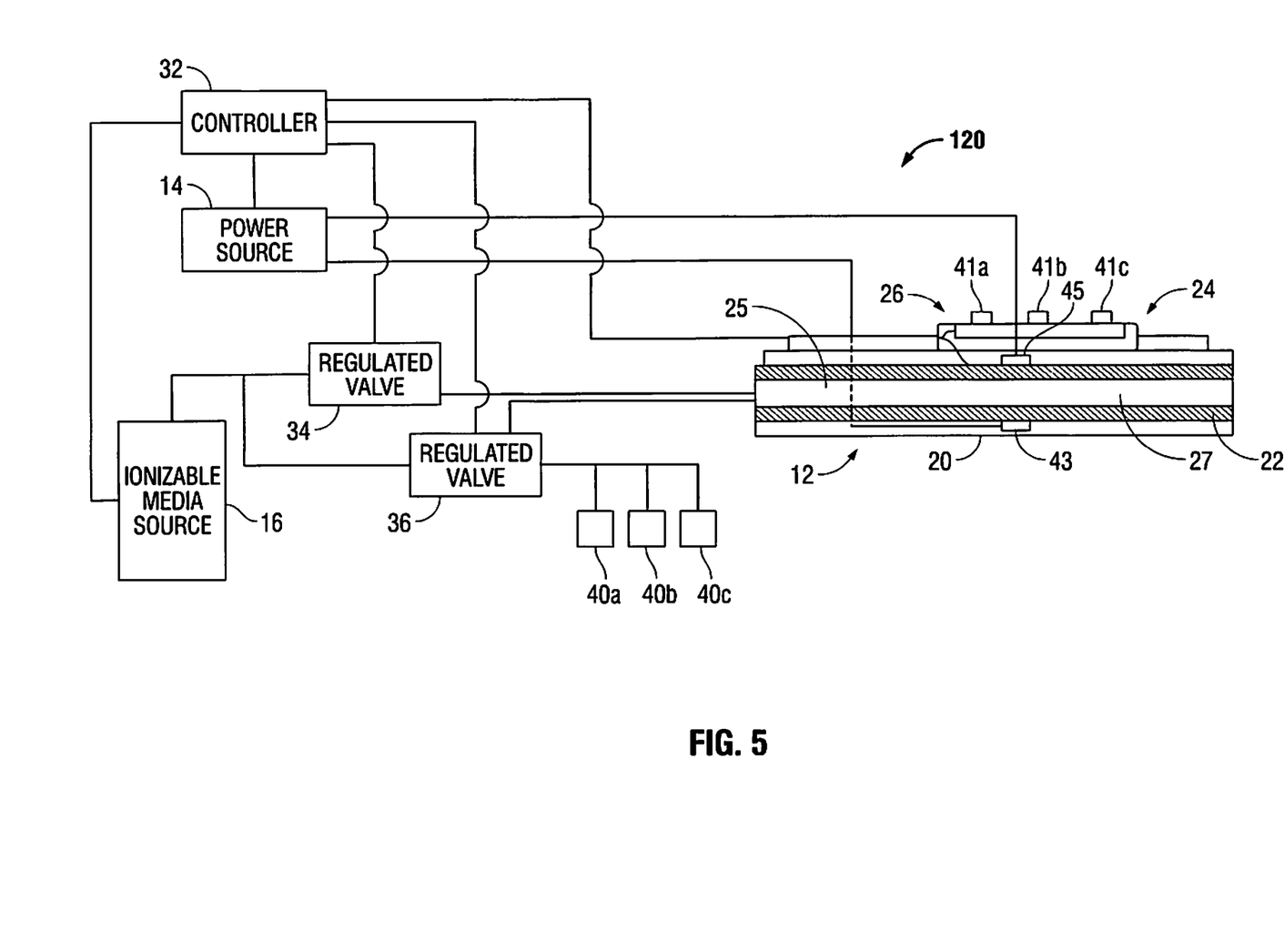
FIG. 5 is a schematic diagram of a plasma system and a plasma handpiece according to another illustrative embodiment the present disclosure.

FIG. 5 shows another embodiment of a plasma system 120 having multiple precursor sources 40a, 40b and 40c, each including various types or combinations of precursors. Multiple precursors may be embodied using any of the above-illustrated containers and/or delivery devices. The input controls 26 may include multiple buttons or switches 41a, 41b and 41c for activating each of the precursor sources 40a, 40b and 40c, respectively. In another embodiment, the input controls 26 may be located at any location in the system 120 where manual operation is desired or in the case of automated systems RF power, flow of ionizable media, and chemical precursors may be controlled automatically by the controller 32 based on a feedback algorithm.

EXAMPLES

Figure 6:
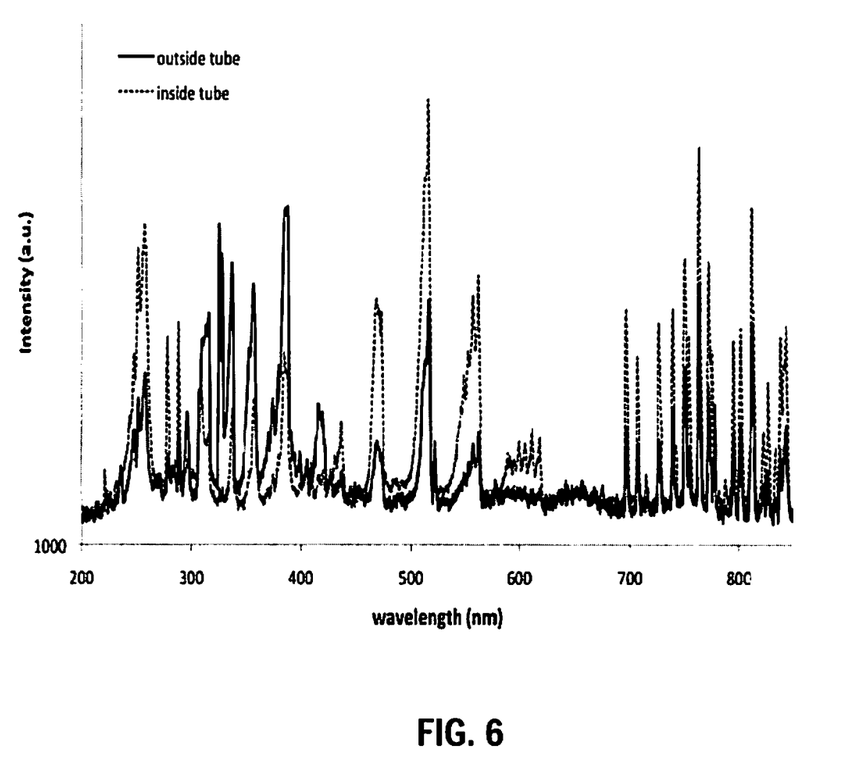
FIG. 6 is spectra graph of a plasma generated according to one illustrative embodiment of the present disclosure.

Argon gas was mixed with $CCl_4$ and ignited within a plasma activation device. Spectra were obtained for the plasma inside outside device as illustrated by the dashed and solid graphs, respectively in FIG. 6. The graphs illustrate generation of various chemical species as a result of the plasma being produced from an ionizable media and a chemical precursor. The intensity of the various emissions correspond to relative concentrations of different chemical species and they show that as the plasma flows into open air, there is a decrease of the density of some species but an increase in the density in other species. This is due to the plasma mixing with nitrogen, oxygen, carbon dioxide and other constituent gases of air. This exemplar plasma was used to successfully to remove tissue material.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure. In particular, as discussed above this allows the tailoring of the relative populations of plasma species to meet needs for the specific process desired on the workpiece surface or in the volume of the reactive plasma.

What is claimed is:

1. An electro surgical system for application of plasma to tissue comprising:
    an electro surgical pencil including:
        a housing including a dielectric tube having an optically reflective coating on an inner surface of the dielectric tube; and
        a removable reactive material coated on the inner surface; and
        an active electrode;
    an ionizable media source configured to supply ionizable media to the electro surgical pencil;
    a precursor source configured to supply at least one precursor feedstock to electro surgical pencil; and
    a power source coupled to the active electrode and configured to ignite the ionizable media, the removable reactive material, and the precursor feedstock at the electro surgical pencil to form a plasma volume, wherein the at least one precursor feedstock and the ionizable media are mixed and ignited concurrently.

2. The electrosurgical system according to claim 1, further comprising a microcontroller for controlling a flow of the ionizable media and the precursor feedstock.

3. The electrosurgical system according to claim 2, further comprising a first regulator valve coupled to the ionizable media source and a second regulator valve coupled to the precursor source, wherein the first and second regulator valves are coupled to the microcontroller.

4. The electrosurgical system according to claim 1, wherein the ionizable media is selected from the group consisting of argon, helium, neon, krypton, xenon, radon, nitrogen, hydrogen, oxygen, carbon dioxide, nitrous oxide, and mixtures thereof.

5. The electrosurgical system according to claim 1, wherein the at least one precursor feedstock is a compound having a functional group selected from the group consisting of acyl halide, alcohol, aldehyde, alkane, alkene, amide, amine, butyl, carboxlic, cyanate, isocyanate, ester, ether, ethyl, halide, haloalkane, hydroxyl, ketone, methyl, nitrate, nitro, nitrile, nitrite, nitroso, peroxide, hydroperoxide, oxygen, hydrogen, nitrogen, and combinations thereof.

6. The electrosurgical system according to claim 1, wherein the at least one precursor feedstock is selected from the group consisting of water, haloalkanes, peroxides, alcohols, amines, alkyls, alkenes, alkalines, and combinations thereof.

7. The electrosurgical system according to claim 1, wherein the precursor source includes at least one of a bubbler, a microfluidic device, a nebulizer, a micropump, a piezoelectric pump, or an ultrasonic vaporizer.

8. The electrosurgical system according to claim 1, wherein the electrosurgical pencil includes a return electrode disposed on an outer surface of the dielectric tube.

9. The electrosurgical system according to claim 8, wherein the active and the return electrodes are capacitively coupled to the plasma volume.

10. An electro surgical system for application of plasma to tissue including:
    an electro surgical pencil including:
        a housing including a dielectric tube having an optically reflective coating on an inner surface of the dielectric tube; and
        a removable reactive material coated on the inner surface; and
        an active electrode;
    an ionizable media source configured to supply ionizable media to the electro surgical pencil;
    a plurality of precursor sources, each of the precursor sources configured to supply at least one precursor feedstock to the electro surgical pencil; and
    a power source coupled to the active electrode and configured to ignite the ionizable media, the removable reactive material, and the precursor feedstock at the electro surgical pencil to form a plasma volume, wherein the at least one precursor feedstock and the ionizable media are mixed and ignited concurrently.

11. The electrosurgical system according to claim 10, wherein the electrosurgical pencil includes input controls to activate each of the plurality of the precursor sources individually.

12. The electrosurgical system according to claim 10, further comprising a microcontroller for controlling a flow of the ionizable media and at least one of the precursor feedstock.

13. The electrosurgical system according to claim 1, wherein the electrosurgical pencil is a hand-held electrosurgical pencil, the power source is an electrosurgical generator, and the plasma volume is configured to at least one of substitute or replace surface-terminating species of biological tissue surfaces.

14. The electrosurgical system according to claim 10, wherein the electrosurgical pencil is a hand-held electrosurgical pencil, the power source is an electrosurgical generator, and the plasma volume is configured to at least one of substitute or replace surface-terminating species of biological tissue surfaces.

* * * * *